United States Patent [19]

Allison et al.

[11] Patent Number: 4,917,922

[45] Date of Patent: Apr. 17, 1990

[54] FLAME RETARDANT PLANT

[75] Inventors: C. Jay Allison, Federal Way; David W. Park, Puyallup, both of Wash.

[73] Assignee: Weyerhaeuser Company, Tacoma, Wash.

[21] Appl. No.: 113,312

[22] Filed: Oct. 28, 1987

[51] Int. Cl.$^4$ .......................... A01G 5/06; A01N 3/00
[52] U.S. Cl. .......................................... 428/22; 156/57; 427/4; 428/921
[58] Field of Search ............ 427/4, DIG. 11; 428/17, 428/21, 22, 921; 156/57

[56] References Cited

U.S. PATENT DOCUMENTS

| | | | |
|---|---|---|---|
| 1,410,226 | 3/1922 | Segall | 427/4 X |
| 1,484,656 | 2/1924 | Koropp et al. | 428/22 |
| 1,714,838 | 5/1929 | Anderson | 8/518 |
| 1,908,922 | 5/1933 | Ruzicka | 47/1 R |
| 2,978,348 | 4/1961 | Fessenden | 427/4 |
| 3,479,211 | 11/1969 | Goldstein | 524/34 |
| 3,537,873 | 11/1970 | Degginger | 428/17 X |
| 3,895,140 | 7/1975 | Sheldon et al. | 428/22 |
| 3,956,538 | 5/1976 | Vartiak | 428/17 X |
| 4,195,139 | 3/1980 | Goulding et al. | 525/441 |
| 4,243,693 | 1/1981 | Nordh | 427/4 |
| 4,248,734 | 2/1981 | Romero-Sierra et al. | 428/22 X |
| 4,278,715 | 7/1981 | Romero Sierra et al. | 428/22 |
| 4,287,222 | 9/1981 | Robinson | 427/4 |
| 4,328,256 | 5/1982 | Romero Sierra et al. | 427/4 |
| 4,365,033 | 12/1982 | Halpern et al. | 524/118 |
| 4,645,682 | 2/1987 | Elmore | 427/4 |
| 4,664,956 | 5/1987 | Dokkestul | 428/22 |
| 4,710,394 | 12/1987 | Sellegaard | 427/4 |
| 4,786,326 | 11/1988 | Grove | 428/921 X |
| 4,788,085 | 11/1988 | DeLuca et al. | 428/18 |
| 4,808,447 | 2/1989 | Baker | 428/17 |

FOREIGN PATENT DOCUMENTS

| | | |
|---|---|---|
| 2124757 | 12/1971 | Fed. Rep. of Germany . |
| 2933438 | 2/1980 | Fed. Rep. of Germany . |
| 1105091 | 11/1955 | France . |
| 1174603 | 3/1959 | France . |
| 2160310 | 6/1973 | France . |

OTHER PUBLICATIONS

Focus on Floriculture, Purdue University, Cooperative Extension Service, vol. 11 (2), May 1983, pp. 8–9.
"The Effects of Additives on Freshness and Flammability of Christmas Trees", John F. Ahrens and George R. Stephens (Connecticut Experimental Station, Bulletin 760, Dec. 1975).

Primary Examiner—Henry F. Epstein

[57] ABSTRACT

A flame retardant plant, having flame retardant material substantially uniformly distributed within the plant. The method of producing such plant involves systemic infusion by contacting a freshly exposed plant surface or cut stem or trunk with an aqueous solution, which contains at least the flame retardant material, for a sufficient period of time. The plant may also contain, along with the flame retardant material, a preservative alone or in combination with a dye, produced by the above method.

16 Claims, No Drawings

FLAME RETARDANT PLANT

FIELD OF THE INVENTION

This invention relates to a flame retardant plant having flame retardant material substantially uniformly distributed within the plant and the method of producing such plant. This invention also relates to a preserved flame retardant plant in which the natural color of the plant is simulated or another color imparted.

BACKGROUND OF THE INVENTION

It is known that flame retardancy of a plant can be accomplished through the use of various chemicals, often complex bromine containing compounds, by means of coating, wetting, injecting, immersing, spraying or some other means of applying the flame retardant chemical to the exterior of the plant. Such exterior application could coincidentally include some penetration of the plant's foliage or shallow penetration of the woody parts, but the methods are predominantly external application. In contrast, the present invention uses a method of systemic infusion which imparts flame retardancy through an internal application.

It is also known that preservation of foliage, parts of plants or plants themselves has been claimed through a process of external immersion, in contrast to the present invention which systemically infuses an aqueous solution. Several patents describe preservation through immersion, such as Sheldon, et al, U.S. Pat. No. 3,895,140; Romero-Sierra et al, U.S. Pat. No. 4,278,715; Romero-Sierra et al, U.S. Pat. No. 4,328,256; Bakker, French Patent 1,105,091 and Barhala, French Patent 2,160,310. All of these listed patents differ from the present invention in that none involve the principal use of systemic infusion and none involve the introduction or treatment of a plant or plant part in any manner with a flame retardant.

A similar process to the present invention is found in Nordh, U.S. Pat. No. 4,243,693. However, the Nordh patent does not teach or suggest the introduction of a flame retardant, but rather merely the introduction of a preservative.

External application of flame retardant materials creates a covering or coating on the plant that is often unattractive and obvious. Thus, methods which externally apply flame retardant material often leave the plant foliage with a chalky, waxy or unnatural looking surface or sticky feeling to the touch.

One of the present inventors is aware of a process for imparting flame retardant property to a plant part. Such previously known process involved the total immersion of a plant part in a solution containing at least 22% by weight of magnesium chloride in combination with approximately 20% glycerin or polyethylene glycol 200 for approximately seven days, rinsing, drying overnight and subsequently dipping the above treated plant part in a coating solution for restoration of color at least partially lost in the previous immersion step. The preferred amount of magnesium chloride in the above process was 27% by weight.

In contrast, the current invention discloses a process for imparting at least flame retardant property to a plant, or plant part, through systemic infusion and using significantly less magnesium chloride to impart flame retardancy. Additionally, the current invention allows simulation of the plant's original color through the use of a dye in the systemically infused aqueous solution without a subsequent coating step.

An article entitled, *The Effects of Additives on Freshness and Flammability of Christmas Trees*, John F. Athrens and George R. Stephens (Connecticut Experiment Station, Bulletin 760, December 1975), teaches away from the use of aqueous chemical additives for the increase in flame retardancy over the use of water alone. The article compared the use of additives such as potassium chloride and material containing ions of potassium, aluminum sulfate, chloride and other chemicals with the use of water alone for measurement of properties including flame retardancy. In the experiments, varieties of trees were placed in water alone, water containing one of the various chemical additives, hot water or allowed to stand without water. The results showed little or no advantage through the use of chemical additives over water alone for flame retardancy.

Lastly, a short publication or bulletin entitled, *Focus on Floriculture,* Purdue University, Cooperative Extension Service, Vol. 11 (2), May 1983, pages 8-9, briefly discusses the use of an ammonium sulfate additive to water used for maintaining a tree, specifically a Christmas tree. This publication does not reflect the present invention since it neither substantiates that the presence of the ammonium sulfate adds to the degree of fire resistance over water only, as evidenced in the above-cited article, nor does the publication reflect the present invention, because of the continued presence of the water and additives in this publication.

The prior art does not teach or suggest the present invention because of the uncertain nature of the uptake of material by a plant. The Nordh patent does not teach or suggest the ability to systemically infuse flame retardant material, since such material differs in characteristics and properties from those materials systemically infused under the Nordh patent. Additionally, other prior art regarding immersion, dipping or spraying do not teach or suggest the present invention since such external applications do not tackle nor solve the problems of internally or systemically infusing material despite the uncertainty of results when dealing with the complex plant vascular system.

Additionally, prior art concerning the addition of material to water to act as a flame retardant either did not show any improvement over the use of water only, which teaches away from this invention, or did not demonstrate flame retardant properties in a plant which had been permanently removed from an aqueous solution or any other source of water.

SUMMARY OF THE INVENTION

The present invention imparts flame retardancy to a plant or plant part, such as limbs with foliage, through systemic infusion, which substantially uniformly disperses the flame retardant material within at least the plant's active xylem and foliage. Such systemic infusion of an aqueous solution containing flame retardant material is accomplished by placing a freshly exposed plant surface or cutend in the flame retardant material as opposed to total immersion of the plant part as in the above previously known processes. The plant is placed in the aqueous solution for a sufficient period of time, which is the time needed to systemically infuse a sufficient amount of aqueous solution to impart some level of flame retardancy to the plant. The aqueous solution is taken up by the plant and substantially uniformly distributed at least within the plant's active xylem and foliage. The plant or plant part must be physiologically active; i.e., it must be capable of imbibing and transporting aqueous liquids at least through the xylem into foliage.

The flame retardant material, which imparts the flame retardant property, reduces the rate of flame spread after exposing a plant containing flame retardant material to an ignition source, compared to a similarly treated plant without flame retardant material. Preferably the plant containing flame retardant material should be self-extinguishing when the ignition source is removed. The flame retardancy test is conducted on a plant, after systemic infusion of the aqueous solution of flame retardant material and after the plant has been removed from the aqueous solution or any other water source and allowed to come to approximate moisture equilibrium with room temperature. The vast majority of the treated plants demonstrated some flame retardancy after removal of a water source and subsequent drying.

Flame retardant materials can include, but are not limited to, alkali-metal bromides, alkaline-earth chlorides or bromides, ammonium salts, boric acid, water soluble salts of boric acid, water soluble cyclic phosphonate esters and mixtures of these materials. Any water soluble material which is capable of imparting flame retardancy is meant to be included in the scope of the invention.

The flame retardant solution infusion rate under the present invention runs from a low of about 0.4 grams of solution per gram of fresh plant weight to a high of about 1.4 grams of solution per gram. The effective range, therefore, is for example 4–30% flame retardant based on fresh plant weight for salts. The effective and preferred ranges differ with each flame retardant material. For example, magnesium chloride as a flame retardant material has a preferred range of 7% to 25% by weight of magnesium chloride and most preferred range of 10–20% by weight. Additionally, the preferred range of concentration in the solution is 10–20% or 15–30% for water soluble cyclic phosphonate esters. It has been found that, in very general terms, the mid range of active ingredient found to be effective is about 13% of the fresh weight, about 15% of the weight in equilibrium with room conditions and about 20% of the final oven dry weight of 65° C. Therefore, the effective range for imparting some flame retardancy is quite broad for each flame retardant material depending on both the material and the plant being treated.

In addition to imparting flame retardant properties, the present invention also discloses a plant which contains a preservative or a preservative and a dye along with the flame retardant material. The preservative maintains the plant in essentially the same original structure and foliage condition, the original structure being the plants original shape and appearance and the foliage condition being the plant's original texture, feel and appearance, except for color. Such preservative materials can include, but are not limited to, glycerin and certain other polyols. In addition, materials such as magnesium chloride and water soluble cyclic phosphonate esters act as both a flame retardant and a preservative. The dye material which may be used with the flame retardant material can be any water soluble material capable of giving a desired color to the plant, which includes the foliage. Foliage color may be similar or identical to the original color or it may be substantially and deliberately changed.

The present invention imparts flame retardancy to a plant or plant part, such as limbs with foliage, without leaving a waxy looking surface or sticky feeling to the touch. Therefore, it is an object of the invention to produce a plant, which term necessarily includes a plant part, such as foliage, with flame retardant properties but without the impression, made by external observation or inspection, of the presence of flame retardant.

It is a further object of the invention to provide such a flame retardant plant through the systemic infusion of flame retardant material which such infusion process involves placing a freshly exposed plant surface or cut end in an aqueous solution containing the flame retardant material.

It is a further object of the invention to provide a preserved flame retardant plant.

It is a further object of the invention to provide a flame retardant plant that along with the flame retardancy, or in combination with the preservative property, also stabilize or imparts a color to the plant, through the use of a dye.

It is a further object of the invention to provide a process for introducing the flame retardant material essentially uniformly into at least the active xylem and foliage of a treatment receptive plant. A treatment receptive plant is a plant which will internally take up the flame retardant, either alone or in combination with a preservative and/or dye, through the process of systemic infusion.

It is a further object of the invention to provide a process for introducing a preservative along with the flame retardant material essentially uniformly into at least the active xylem and foliage of a treatment receptive plant.

It is a further object of the invention to provide a process for introducing a dye either along with the flame retardant material alone or in conjunction with a preservative, essentially uniformly into at least the active xylem and foliage of a treatment receptive plant.

Other objects will become clear from the following specification of the invention.

DETAILED DESCRIPTION OF THE INVENTION

It is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate art, and not as limiting upon the present invention.

Several flame retardant materials can be used in the following described process, and plant produced therefrom. Therefore, the flame retardant materials described in the following examples are meant for illustrative purposes and not for limiting the breadth and scope of this invention.

Similarly, the preservative and dye materials described in the following examples are meant for illustrative purposes.

EXAMPLE 1

Flame Retardancy Test

The treated plant specimen is tested using the following apparatus. A sheet metal cabinet 30×30 cm in cross section and 76 cm high is provided to protect the specimen from drafts. The shield has a perforated top and baffle, and has a hinged glass front portion. The hinged glass front provides access for inserting the test specimens. The ignition source is a Tirril-type laboratory gas burner with a 9.5 mm diameter tube. The air supply vents to the burner are completely closed during tests. Gas supply is adjusted to give a luminous flame 38 mm high. The test apparatus and procedures are generally as described in Federal Test Method Std. No. 191A, Method 5903.

The specimens are suspended vertically within the shield so that their tips are 19 mm above the top of the burner tube. The flame is applied for 12 seconds and then withdrawn. Flame duration after withdrawal of the ignition source and time to extinction of any afterglow are noted, as is the length of char on the specimens. An estimate of the percentage of sample consumed may also be made. A specimen is regarded as self-extinguishing if, after ignition source withdrawal, flaming ceases before the flame has traveled from bottom to top of the specimen. If continuous bottom-to-top burning has occurred at any place on a specimen, it is not considered to be self-extinguishing, even if the entire specimen has not been consumed.

EXAMPLE 2

Control Preservative Solution BG

A preservative solution intended to give a natural appearing bluish-green foliage color was made as follows. All components are given as percentage by weight. This solution is similar to that taught by Nordh in U.S. Pat. No. 4,243,693.

| | |
|---|---|
| Glycerin (96%) | 30.83% |
| Water | 67.80 |
| Potassium Nitrate | 0.55 |
| Citric Acid | 0.012 |
| C.I. Acid Yellow 23[1] | 0.68 |
| C.I. Acid Blue 3[2] | 0.12 |
| Biocide[3] | trace |
| | 99.99+% |

[1]C.I. 19140. Also called Tartrazine, F.D.&C. Yellow No. 5, and Food Yellow 4.
[2]C.I. 42651. Also called Patent Blue V.
[3]8-hydroxyquinoline sulfate, 13 mg/L.

Plants to be preserved are severed above the rootline of a living plant. Alternatively, a portion of a plant such as a limb may be used. The freshly cut end is immersed in the above solution and allowed to remain for a period of about 3–14 days at a temperature of about 20°–40° C. and relative humidity of about 40–85%. The length of treatment time depends on the nature (species, variety, season, etc.) of the particular plant being treated.

It is believed treatment solution is imbibed and transported through at least the active xylem tissue of the plant into the foliage. The preserved plant retains foliage tightly and has a feel and appearance similar or nearly identical to the living plant. It may be necessary to vary treatment conditions other than time, depending on the species or cultivar, since there is a great difference in response between different plants. Many plants are preserved readily but some, especially those from a number of coniferous genera, only with difficulty.

Other materials besides those listed may frequently be substituted with satisfactory effect. Glycerin and certain other polyols have good preservative properties. Many other water soluble dyes may be substituted for those named above.

Preserved plants treated with the above solutions and allowed to dry to equilibrium with ambient conditions will generally ignite when exposed to a direct flame and will usually continue to burn when the ignition source is removed. In fact, the preservative materials themselves are significant contributors to the fuel load.

EXAMPLE 3

A preferred flame retardant material is a water soluble member of the group broadly defined as water soluble cyclic phosphonate esters. These are generally prepared by reacting alkyl-halogen free esters with a bicyclic phosphite. Examples of suitable materials are as follows:

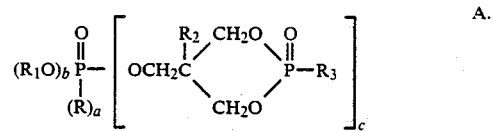
A.

where a is 0, 1, or 2, b is 0, 1, or 2, C is 1, 2, or 3 and a+b+c is 3; R and $R_1$ are alkyl, alkoxy, aryl, aryloxy, alkaryl, alkaryloxy, aralkyl, aryloxy-alkoxy, or aralkoxy wherein the alkyl portion of these groups may contain hydroxyl but not halogen and the aryl portion may contain chlorine, bromine and hydroxyl groups; $R_2$ is alkyl, hydroxy-alkyl, or aryl; $R_3$ is lower alkyl ($C_1$–$C_4$) or hydroxyalkyl ($C_1$–$C_4$);

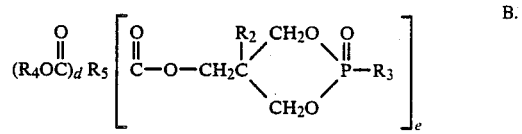
B.

where d is 0, 1, or 2; e is 1, 2, or 3; d+e is 3; $R_2$ is as defined above, $R_3$ is as defined above, $R_4$ is alkyl, aryl, alkaryl, aralkyl, or aryloxyalkyl, wherein the aryl portion may contain bromine, chlorine or hydroxyl; and $R_5$ is monovalent, divalent or tervalent alkyl, alkylene, aryl, or arylene radical wherein the aryl or arylene radical may contain bromine, chlorine, alkyl or hydroxy groups; and

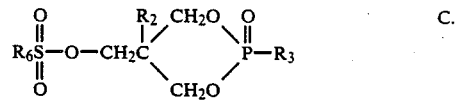
C.

where $R_2$ and $R_3$ are as defined above; and $R_6$ is alkyl, aryl, alkylaryl, or arylalkyl wherein the aryl portion may contain bromine, chlorine or hydroxyl.

Preparation of these materials is described in Anderson et al, U.S. Pat. No. 3,789,091.

A preferred material is defined by formula A where a is 1, b is 0 or 1, and c is 2−b; R, $R_1$, and $R_3$ are methyl and $R_2$ is ethyl. This is shown by the formula.

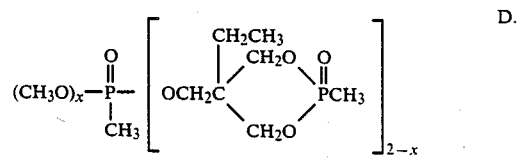
D.

where x is 0 or 1.

The preferred composition is available as Antiblaze 19 or Antiblaze 19T from Albright and Wilson, Inc., Richmond, Va. Antiblaze is a registered trademark of the above supplier.

Surprisingly, the water soluble cyclic phosphonate esters have excellent plant preservative properties, in addition to their contribution of flame retardancy. This excellent plant preservative property was unexpected and the reasons for this are not yet fully understood. As the following examples will show, these compounds are effective, not only in addition to or as a substitute for a portion of the polyhydroxy preservative material, but as the sole preservative.

EXAMPLE 4

Two treatment solutions were made up as follows. In the first (Solution A), 382 g of Antiblaze 19T (93% water soluble cyclic phosphonate ester) was added to 606 g of BG control solution. To this mixture was further added 260 g of water and 229 g of 0.5M KOH to bring the pH up to 5.2. The final solution contained 14.5% glycerin and 15.1% Antiblaze, both expressed by weight on an as received basis. The second treatment solution (Solution B) had 382 g Antiblaze 19T, 809 g of 0.5M KOH, 7.2 g $KNO_3$, and 1.8 g of C.I. Acid red 52 (C.I. No. 45100). The pH was 4.7 and Antiblaze content 31.8% on an as received basis.

Three plant species treated were limbs of European beech, *Fagus sylvaticus* and Bluepoint juniper, *Juniperus chinensis*, var. "Bluepoint." Leaves of common beargrass, *Xerophyum tenax* (Pursh.) Nutt., were severed from the plant at their bases and formed into bundles for treating.

The freshly cut ends were immersed in the respective solutions and treated at 35° C. and 60% R.H., removed and then conditioned at 21° C. and 20% R.H. and 50% R.H. for the number of days noted.

|  | Treatment days | Conditioning days | |
| --- | --- | --- | --- |
|  |  | 20% R.H. | 50% R.H. |
| Beech | 7 | 2 | 3 |
| Juniper | 6 | 3 | 4 |
| Beargrass | 2 | 4 | 3 |

Due to lack of available samples no juniper was treated in Solution B or in the BG Control solution (however, see the following example). Samples were then tested for flame retardancy. Results of tests are given in the following table.

TABLE I

|  | B.G. Control | Solution A | Solution B |
| --- | --- | --- | --- |
| Beech | | | |
| Solution takeup[1] | —[3] | 0.90 | 0.77 |
| Appearance[2] | 4+ | 4 | 2 |
| Flame duration, sec. | 25 | 0 | 0 |
| Char length, cm | — | 11 | 10 |
| % Consumed | 100 | — | — |
| Self-extinguishing | No | Yes | Yes |
| Beargrass | | | |
| Solution takeup | 0.60 | 0.36 | — |
| Appearance | 5 | 5 | — |
| Flame duration, sec. | 29 | 4/55[4] | 1 |
| Char length, cm | — | — | 7 |
| % Consumed | 100 | 40/80[4] | — |
| Self-extinguishing | No | Yes, No | Yes |
| Juniper | | | |
| Solution takeup |  | 0.65 |  |

TABLE I-continued

|  | B.G. Control | Solution A | Solution B |
| --- | --- | --- | --- |
| Appearance |  | 4+ |  |
| Flame duration, sec. |  | 3 |  |
| Char length, cm |  | 8 |  |
| % Consumed |  | — |  |
| Self-extinguishing |  | No |  |

[1]Measured as grams solutions/grams fresh plant weight.
[2]Appearance Ratings:
1. Totally dry and untreated.
2. Dye in foliage mid veins, foliage otherwise mostly dry.
3. Foliage mostly treated. Some mottling and/or slighly dry.
4. Well treated with only slight discoloration.
5. Well treated, good color and uniformity.
[3]A dash means data not available.
[4]Considerable variability between replicate test results.

There is no good explanation of the inconsistency between replicate tests of the beargrass other than to note that because of its physical form and difficulty to treatment, it is difficult to use in the testing apparatus.

EXAMPLE 5

The following three preservative-flame retardant solutions were made for testing.

|  | Solution C | Solution D | Solution E |
| --- | --- | --- | --- |
| Glycerin (96%) | 15.85 | — | — |
| Water | 67.80 | 84.33 | 69.44 |
| Citric Acid | 0.0115 | — | — |
| Potassium nitrate | 0.0553 | — | — |
| C.I. acid Yellow 23 | 0.68 | 0.67 | 0.67 |
| C.I. Acid Blue 3 | 0.12 | 0.12 | 0.12 |
| Antiblaze 19T (93%) | 15.00 | 14.88 | 29.76 |
| Potassium hydroxide to give | pH 4.5–5.0 | pH 4.7 | pH 4.7 |
| Biocide | trace | trace | trace |

Antiblaze was initially made up as a 50% water solution and the pH was then adjusted with aqueous KOH.

European beech and Bluepoint juniper were used, as in the previous example. Two treatment conditions were used. Treatment 1 was for five days at 22° C. and ambient humidity (approximately 50%). Treatment 2 was for five days at 33° C. and 80% R.H. Treated samples were then conditioned for three days at 20% R.H. and three days at 50% R.H., both at 21° C., prior to testing. Both treatments were used for beech but only Treatment 2 for juniper. In view of normal practice dictating a maximum of 60% R.H. during treatment, Treatment 2 might be considered by those skilled in the art as being suboptimal.

Flame retardancy tests gave the following results.

TABLE II

|  | BG Control | Solution C | Solution D | Solution E |
| --- | --- | --- | --- | --- |
| Treatment No. 1 | | | | |
| Beech | | | | |
| Solution takeup | 0.85 | 0.79 | 0.75 | 0.63 |
| Appearance | 5 | 4+ | 3+ | 4 |
| Flame duration, sec | 8 | 1 | 0 | 0 |
| Char length, cm | — | 8 | 7 | 9 |
| % Consumed | 100 | — | — | — |
| Self extinguishing | No | Yes | Yes | Yes |
| Treatment No. 2 | | | | |
| Beech | | | | |
| Appearance | 5 | 4+ | 4 | 3+ |
| Flame duration, sec. | 6 | 1 | 0 | 0 |
| Char length, cm | — | 7 | 10 | 9 |
| % Consumed | 80 | — | — | — |
| Self extinguishing | No | Yes | Yes | Yes |
| Juniper | | | | |

TABLE II-continued

| | BG Control | Solution C | Solution D | Solution E |
|---|---|---|---|---|
| Appearance | 4+ | 5 | 5 | 3+ |
| Flame duration, sec. | 36 | 6 | 1 | 1 |
| Char length, cm | — | 9 | 10 | 6 |
| % Consumed | 100 | — | — | — |
| Self-extinguishing | No | Yes | Yes | Yes |

It is immediately evident from the data that all of the treatments using the water soluble cyclic phosphonate esters give plant specimens generally having good to excellent appearance and very good flame retardancy. Treated specimens made with the control solution have very poor flame retardancy and, once ignited, are usually totally consumed in a self-sustaining fire.

EXAMPLE 6

Water soluble cyclic phosphonate esters can be used in conjunction with inorganic salts to give preserved plants having good appearance and flame resistance. A solution having the following composition was made up.

| | |
|---|---|
| Glycerin (96%) | 13.62% |
| Water | 63.15 |
| Potassium nitrate | 0.41 |
| Citric acid | 0.008 |
| C.I. Acid yellow 23 | 0.50 |
| C.I. Acid blue 3 | 0.089 |
| Magnesium chloride hexahydrate | 9.19 |
| Antiblaze 19T (93%) | 13.03 |
| KOH to give pH of | 4.6 |
| Biocide | trace |

Four plant species were treated by placing their freshly cut ends in the above solution. These were Canary Island date palm, *Phoenix canariensis*; eucalypt, *Eucalyptus gunnii*; vine maple, *Acer circinatum*, and sycamore *Platanus acerifolia*, the latter also being known as London plane tree. Vine maple is known as a species that is difficult to preserve. Sycamore and vine maple were treated for three days at 33° C. and 60% R.H. then conditioned at 20% R.H. for three days and 50% R.H. for three days, each at 21° C. The palm and eucalyptus were treated for six days at 33° C. and 60% R.H., then conditioned at 20% R.H. for two days and 50% R.H. for one day, both at 21° C., prior to testing. Test results for flame retardancy were as follows:

TABLE III

| | Palm | Eucalyptus | Vine Maple | Sycamore |
|---|---|---|---|---|
| Appearance | 4+ | 3+ | 2 | 4+ |
| Flame duration, sec. | 0 | 31 | 0 | 6 |
| Char length, cm | 3 | — | 17 | 13 |
| % Consumed | — | 65 | — | — |
| Self-extinguishing | Yes | No | No | Yes |

Neither the vine maple or eucalyptus could be considered to have satisfactory flame resistance. Appearance of the vine maple was poor and only marginal for eucalyptus. However, the palm and sycamore both had excellent appearance and flame retardancy. This shows that some important foliage species can be effectively preserved and made flame retardant using a mixture of water soluble cyclic of phosphonate ester and an inorganic salt.

EXAMPLE 7

Use of Salts as Flame Retardants

A selected group of inorganic salts appear to be effective in contributing flame retardancy. In the following example, these inorganic salts are used in conjunction with a polyhydroxy preservative material. It has been essentially unpredictable as to which salts would be effective and which salts were not. In many cases the salts were actually deleterious, not only failing to contribute flame resistance but adversely affecting preservation of the plants being treated. The following examples show cases in which fair to good flame retardancy and preservation were obtained using inorganic salts in the preservative solution.

To 100 mL of BG Control solution was added the amounts of three fire retardant salts shown in the following table. The salts used were ammonium dihydrogen phosphate, sodium bromide and a 50:50 parts by weight mixture of these two salts.

Freshly cut ends of 50–100 cm long branches of western red cedar (*Thuja plicata* D. Don) were immersed five days in the above salt solutions and in the BG Control solution in a treatment chamber held at 35° C. and 60% R.H. Three or four specimens were treated in each solution. The treated specimens were conditioned after treatment for nine days at about 21° C. and ambient humidity prior to testing. Fire tests were then carried out as described in Example 1 with the following results.

TABLE IV

| Sample | A | B | C | D |
|---|---|---|---|---|
| Flame retardant | None | $NH_4H_2PO_4$ | NaBr | $NH_4H_2PO_4$ |
| Concentration of retardant, of BG control solution, g/100 mL | — | 25 | 30 | 40 |
| Concentration of retardant % | — | 18.8 | 21.7 | 27.0 |
| Flame duration, sec. | 36 | 2 | — | — |
| Char length, cm | 12 | 2 | 0 | 0 |
| % Consumed | >50 | <10 | <10 | <10 |
| Appearance rating[1] | 3 | 2 | 3 | 2 |

EXAMPLE 8

Flame Retardant Efficacy of Calcium Chloride

As was done in the previous example, calcium chloride dihydrate was added to the BG Control solution in varying amounts, as shown in the table below. Samples of salal, *Gaultheria shallon* Pursh, English ivy, *Hedera helix*, and an ornamental juniper, *Juniperus chinensis* var. "Bluepoint" were treated in the solutions for four days at 30° C. and 60% R.H. Treated samples were then conditioned for three days at 20% R.H. and one day at 50% R.H., both at 21° C.

Salt concentrations used and the results of fire tests are given in the following table.

TABLE V

| | | | | | |
|---|---|---|---|---|---|
| $CaCl_2.2H_2O$/100 mL BG Control | 0 | 10 | 20 | 30 | 40 |
| % $CaCl_2.2H_2O$ in treating Solution | 0 | 8.4 | 15.6 | 21.7 | 27.0 |
| % Glycerin (95%) in treating Solution | 30.8 | 28.2 | 26.0 | 24.2 | 22.5 |
| | | Salal | | | |
| Appearance | 3 | 3 | 2 | 2 | 1 |
| Flame duration, sec. | 19 | 7 | 0 | 1 | 0 |

TABLE V-continued

| | | | | | |
|---|---|---|---|---|---|
| Char length, cm | — | 10 | 5 | 3 | 5 |
| % Consumed | 100 | 60 | — | — | — |
| Self-extinguishing | No | No | Yes | Yes | Yes |
| *Ivy* | | | | | |
| Appearance | 4 | 4 | 2 | 2 | 1 |
| Flame duration, sec. | 13 | 8 | 3 | 2 | 5 |
| Char length, cm | — | 6 | 4 | 3 | 4 |
| % Consumed | 60 | — | — | — | — |
| Self-extinguishing | No | Yes | Yes | Yes | Yes |
| *Juniper* | | | | | |
| Appearance | 4 | 4 | 4 | 1 | 1 |
| Flame duration, sec. | 73 | 67 | 37 | 54 | 46 |
| Char length, cm | — | — | 9 | (1) | (2) |
| % Consumed | 100 | 100 | — | (1) | (2) |
| Self-extinguishing | No | No | Yes | (1) | (2) |

(1) Inconsistent. One sample self-extinguishing, 8 cm char length. Two samples 100% consumed.
(2) Inconsistent. Two samples self-extinguishing, 10 cm char length. One sample 100% consumed.

In general, for all samples in this group appearance was poorer as the concentration of calcium chloride increased. This may be due to the relatively lower concentration of preservation in the solutions with higher inorganic salt content. For the above and other examples the most useful range of salt concentration in the preservation solution appears to be about 8–22%.

The close chemical homolog, calcium bromide, was not tested but would be expected to perform in similar fashion.

EXAMPLE 9

Flame Retardant Efficiency of Ammonium Salts

As was done in the previous example, five different ammonium salts were added to BG Control solution. In all cases the salt was added in a ratio of 20 g to 100 mL of BG Control solution to give a concentration of 15.6% ammonium salt and 26.0% glycerin in the ultimate treating solution. The plant treated in all cases was salal (*Gaultheria shallon* Pursh.). Freshly cut ends were placed in the treatment solution for the indicated time in a treatment chamber held at 35° C. and 60% R.H. The treated plants were then conditioned at 21° C. for the times noted in the following table. The left hand figure in the column beneath each salt represents a plant treated with BC Control solution.

TABLE VI

| Salt Used | $NH_4Cl$ | $NH_4OSO_2NH_2$ | $(NH_4)_2SO_4$ | $NH_4H_2PO_4$ | $(NH_4)_2HPO_4$ |
|---|---|---|---|---|---|
| Treatment time, days | 4 | 4 | 4 | 3 | 4 |
| Conditioning, days at 20% R.H. | 2 | 2 | 3 | 4 | 3 |
| Conditioning, days at 50% R.H. | 3 | 3 | 3 | 3 | 1 |
| Appearance | 5/4 | 4/3 | 2/1 | 2/1 | 2/1 |
| Flame duration, sec. | 7/0 | 11/0 | 2/0 | 8/0 | 4/1 |
| Char length, cm | —/5 | —/5 | —/4 | —/5 | — |
| % Consumed | 90/— | 90/— | 100/— | 100/— | 100/— |
| Self-extinguishing | No/Yes | No/Yes | No/Yes | No/Yes | No/Yes |

Runs with the various salts were made at different times although a separate BG Control sample was run simultaneously with each salt. The reasons for the poor appearance of the last three runs for both the control and flame retardant samples are unclear.

EXAMPLE 10

Sodium Borate as Flame Retardant

Western red cedar (*Thuja plicata* D. Don) was treated using two concentrations of sodium tetraborate decahydrate in a red preservative solution. The limb samples were in treatment for eight days in an environment at 35° C. and 60% R.H. and then were conditioned in an ambient room environment (approximately 21° C. at 50–70% R.H.) for nine days.

The red preservative solutions were made as follows. The results of burning tests are also noted in the Table.

TABLE VII

| Solution | Red Control | A | B |
|---|---|---|---|
| Glycerin (96%) | 30.00 | 27.47 | 25.33 |
| Water | 69.28 | 63.43 | 58.49 |
| Potassium Nitrate | 0.555 | 0.508 | 0.469 |
| Citric Acid | 0.0083 | 0.0076 | 0.0070 |
| C.I. Acid red 52 | 0.152 | 0.139 | 0.128 |
| $Na_2B_4O_7.10H_2O$ | 0 | 8.44 | 15.56 |
| Biocide | Trace | Trace | Trace |
| *Flame Retardant Tests* | | | |
| Appearance | 5 | 4 | 4 |
| Flame duration, sec. | — | 5 | 3 |
| Char length, cm | — | 2 | 2 |
| % Consumed | 100 | — | — |
| Self-extinguishing | No | Yes | Yes |

Sodium borate, like all of the other salts tested, appears to have some species specificity in regard to contribution to flame retardancy. The above results on western red cedar were excellent. Similar tests run on salal and Bluepoint juniper gave poorer appearance and flame retardancy.

EXAMPLE 11

Use of Magnesium Chloride as Flame Retardant

Magnesium chloride hexahydrate was added in varying amounts to BG Control solution, as shown in the following table. Salal and western red cedar were treated by immersing their freshly cut ends for four days in a treatment chamber held at 35° C. Treated samples were then conditioned two days at 20% R.H. and one day at 50%, both at 21° C., before testing.

TABLE VIII

| $MgCl_2.6H_2O$ mL BG Control | 0 | 10 | 20 | 30 | 40 |
|---|---|---|---|---|---|
| % $MgCl_2.6H_2O$ in treating solution | 0 | 8.4 | 12.5 | 21.7 | 27.0 |
| % Glycerine (96%) in treating solution | 30.8 | 28.2 | 26.0 | 24.2 | 22.5 |
| *Salal* | | | | | |
| Appearance | 3 | 4 | 3 | 2 | 2 |

TABLE VIII-continued

| | | | | | |
|---|---|---|---|---|---|
| Flame duration, sec. | 5 | 0 | 0 | 0 | 0 |
| Char length, cm | — | 7 | 3 | 3 | 1 |
| % Consumed | 100 | — | — | — | — |
| Self-extinguishing | No | Yes | Yes | Yes | Yes |
| | | Red Cedar | | | |
| Appearance | 4 | 4 | 4 | 2 | 2 |
| Flame duration, sec | 20 | 3 | 1 | 2 | 2 |
| Char length, cm | — | 3 | 4 | 3 | 3 |
| % Consumed | 100 | — | — | — | — |
| Self-extinguishing | No | Yes | Yes | Yes | Yes |

Magnesium chloride is an effective flame retardant for these species in all concentrations tested. Appearance of highest usages of the salt was adversely affected.

Similar results to those reported in this example were achieved using white birch, *Betula alba;* English ivy, *Hedera helix;* the ornamental juniper, *Juniperus chinensis* var. "Bluepoint"; Canary Island palm, *Phoenix canariensis;* and sycamore (London plane tree), *Platanus acerifolia*. In all cases with the latter group of trees the treatment solution had 15 g MgCl$_2$.6H$_2$O/100 mL of BG Control solution, a concentration of MgCl$_2$.6H$_2$O of 12.1%. This shows the process of producing preserved flame retardant foliage to be applicable to a wide variety of plant species.

EXAMPLE 12

There are indications that many plants are able to take up only some limiting amount of chemical additions; i.e., preservatives and flame retardant salts. Thus, if the amount of flame retardant salts is high in the treating solution, a relatively lower amount of preservative chemicals will be taken up. Stated otherwise, the effects of flame retardant and preservative materials does not generally appear to be additive. Flame retardancy is frequently gained at the expense of preservation quality. It is often necessary to arrive at a balance between the properties if a satisfactory product is to be obtained. A notable exception to this generalization is the case when the flame retardant also acts in whole or in part as a preservative, as was shown earlier using the water soluble cyclic phosphonate esters.

The following flame retardant/preservative solutions were made up in which magnesium chloride hexahydrate replaced 40% and 50% of the glycerin in the BC Control preservative solution.

| Solutions | BG Control | A | B |
|---|---|---|---|
| Glycerin (96%) | 30.83 | 18.42 | 15.42 |
| Water | 67.80 | 67.78 | 67.78 |
| Potassium Nitrate | 0.55 | 0.55 | 0.55 |
| Citric Acid | 0.012 | 0.012 | 0.012 |
| C.I. Acid Yellow 23 | 0.68 | 0.68 | 0.68 |
| C.I. Acid Blue 3 | 0.12 | 0.12 | 0.12 |
| Magnesium chloride.6H$_2$O | 0 | 12.4 | 15.41 |
| Biocide | trace | trace | trace |

Freshly cut ends of the ornamental juniper, *Juniperus chinensis* var. "Bluepoint"; the palm *Phoenix canariensis;* and quaking aspen, *Populus tremuloides* were placed in the solutions and treated and conditioned as shown in the following table. The juniper was in the form of entire small trees. Branches or branch portions were used for aspen and fronds severed adjacent the trunk were used in the case of Canary Island date palm. BC Control treated samples were made using the same conditions outlined for Solutions A and B.

TABLE IX

| Sample Treatment Conditions | | | |
|---|---|---|---|
| | Aspen | Juniper | Palm |
| Treatment, days/°C./% R.H. | 5/23/60 | 4/35/60 | 4/35/65 |
| Conditioning[1], days at 20% R.H. | 3 | 2 | 2 |
| Conditioning[1], days at 50% R.H. | 2 | 1 | 1 |

[1]At 21° C.

Treated samples were flame tested with the following results.

TABLE X

| Species | Aspen | | | Juniper | | | Palm | |
|---|---|---|---|---|---|---|---|---|
| Treatment | Cont | A | B | Cont | A | B | Cont | A |
| Appearance | 4 | 3+ | 2 | + | 4 | 4 | 5 | 4 |
| Pickup, g/g | 0.86 | 0.93 | 0.68 | 0.96 | 0.77 | 0.72 | 0.94 | 0.60 |
| Flame duration sec. | 22 | 0 | 2 | >90 | 12 | 4 | 46 | 1 |
| Char length, cm | — | 2 | 4 | — | 9 | 5 | — | 5 |
| % Consumed | ~90 | — | — | 100 | — | — | 50 | — |
| Self-extinguishing | No | Yes | Yes | No | Yes | Yes | No | Yes |

The efficiency of the treatment is immediately evident with excellent flame retardancy and generally only minor deterioration in appearance. Flame retardancy of all the BC Control treated samples was poor.

EXAMPLE 13

Magnesium chloride is unusual in that it is the one salt known to the inventors which is effective both as a flame retardant and a preservative. To show this, short limb portions of two species, *Juniperus chinensis* var. "Torulosa" and the sycamore *Platanus acerifolia*, were treated with the following solutions. Each solution had 0.15% Rhodamine B dye (C.I. Acid red 52) as the only additive other than the materials noted in the table. Freshly cut ends were immersed for five days in an environment at 30° C. and 60% R.H. Treated samples were then conditioned for two days at 20% R.H. and three days at 50% R.H., both at 21° C.

TABLE XI

| | A | B | C |
|---|---|---|---|
| Solution | Water | 15% | 15% |
| Preservative | only | MgCl$_2$.6H$_2$O | Antiblaze 19T |
| | Juniper | | |
| Flame duration, sec. | 2 | 0/14[1] | 1 |
| Afterglow time, sec. | 16 | 2/180+ | 0 |
| Char length, cm | 5 | 2/16 | 9 |
| Self-extinguishing | Yes | Yes/No | Yes |
| Appearance after conditioning | Sl. dry, no color | Sl. dry, abt. 50% color | Sl. dry, uniformly colored |
| Appearance after 45 days | Dry, olive green, brittle | Dry, sl. brittle | Mod dry, mod. brittle good color |
| | Sycamore | | |
| Flame duration, sec. | 0[2] | 0 | 0 |
| Afterglow time, sec. | 180+ | 6 | 0 |
| Char length, cm | — | 5 | 9 |
| Self-extinguishing | No | Yes | Yes |
| Appearance after conditioning | Dry, curled | Soft, flexible no curl, uniform color | Soft, flexible 90-100% color |
| Appearance After 45 days | Dry, curled | Soft, flexible, no curl | Sl.dry,sl. curl, flexible |

TABLE XI-continued

| Solution<br>Preservative | A<br>Water<br>only | B<br>15%<br>MgCl$_2$.6H$_2$O | C<br>15%<br>Antiblaze 19T |
|---|---|---|---|
| | | | brittle |

(1)Left column run on red dyed portions/right column run on undyed portions of samples.
(2)Totally consumed during 12 sec. flame exposure "Torulosa" variety juniper is rather difficult to preserve and past results have been of variable quality. This may account for the lack of dye (and presumably water) takeup in the A solution samples and the variable results with the B solution samples.

While the results with the juniper were equivocal, magnesium chloride is seen to be effective both as a preservative and flame retardant for the sycamore.

EXAMPLE 14

Samples Treated by Total Immersion

One known prior art flame retardant/preservative treatment involved total immersion of the plant in a rather concentrated magnesium chloride or magnesium chloride/glycerin solution. It was necessary to after treat plants so treated using an external dye to restore color. Most typically a dyed flame retardant coating would be applied. The present inventors regard the products produced by this two-step process to be different in kind from those described herein.

To demonstrate the inferiority of the immersion process branches of *Juniperus chinensis* var. "Torulosa" were completely immersed in the following solution (see also example 12A)

| Glycerin (96%) | 18.48% |
|---|---|
| Water | 68.03 |
| Potassium nitrate | 0.55 |
| Citric acid | 0.012 |
| C.I. Acid yellow 23 | 0.47 |
| C.I. Acid blue 3 | 0.018 |
| Magnesium chloride.6H$_2$O | 12.44 |

Dye concentration here was adjusted slightly to give a "medium blue green" foliage color. The branches were held in the solution for six days at 30° C. They were then removed and drained and then conditioned for two days at 20% R.H. and three days at 50% R.H., both at 21° C. The samples were held an additional two days at room conditions of about 21°-22° C. and 50-60% R.H. before testing.

Flame retardancy tests were as follows:

| Appearance | 2 |
|---|---|
| Estimated solution pickup g/g | 0.31 |
| Flame duration, sec. | 2 |
| Char length, cm | 6 |
| Self-extinguishing | Yes |

The sample appearance was generally poor, with predominantly yellowed foliage having occasional areas where some dye had been absorbed. This is in comparison with samples similarly treated in which only a cut end of a branch had been immersed in the solution. Those samples were uniformly colored with an appearance rating of 4-5 and similar flame resistance to the ones tested above. All indications point to a relatively superficial treatment of the immersed samples compared with a systemic treatment for those in which only a cut end was placed in the solution.

It is understood that an external application of flame retardant may also be used on a plant which has been treated as described in this invention.

I claim:

1. A flame retardant plant having foliage and structure which comprises a plant or a plant portion, not attached to a water source, having infused therein an effective amount of flame retardant material essentially uniformly distributed at least within the active xylem and the foliage.

2. The product of claim 1 which further includes a preservative essentially uniformly distributed at least within the active xylem and foliage, said preservative serving to maintain the plant in essentially the same original structure and foliage condition.

3. The product of claim 1 which further includes a dye essentially uniformly distributed at least within the active xylem and the foliage, said dye serving to give a desired foliage color.

4. The product of claim 3 which further includes a preservative essentially uniformly distributed at least within the active xylem and the foliage.

5. The product of claim 1 in which the flame retardant material also is a preservative.

6. The product of claim 5 in which the flame retardant material is magnesium chloride.

7. The product of claim 5 in which the flame retardant material is water soluble cyclic phosphonate ester.

8. The product of claim 1 in which the flame retardant material is selected from the group consisting of alkali-metal bromides, alkaline-earth chlorides or bromides, ammonium salts, boric acid, water soluble salts or boric acid, water soluble cyclic phosphonate esters and mixtures thereof.

9. The product of claim 1 in which the flame retardant material is selected from the group consisting of alkali-metal bromides, alkaline-earth chlorides or bromides, water soluble cyclic phosphonate esters and mixtures thereof.

10. The product of claim 1 in which the flame retardant material is selected from the group consisting of ammonium salts, boric acid, water soluble salts of boric acid and mixtures thereof.

11. The product of claim 1 in which the flame retardant material is selected from the group consisting of sodium bromide, potassium bromide and mixtures thereof.

12. The product of claim 1 in which the flame retardant is an alkaline-earth halide with the formula: XY$_2$, in which X is calcium or magnesium and Y is bromine or chlorine.

13. The product of claim 1 in which the flame retardant material is magnesium chloride.

14. The product of claim 1 in which the flame retardant is sodium bromide.

15. The product of claim 1 in which the flame retardant is posassium bromide.

16. The produce of claim 1 in which the flame retardant is water soluble cyclic phosphonate ester.

* * * * *